United States Patent
Qu et al.

(10) Patent No.: US 10,184,837 B2
(45) Date of Patent: Jan. 22, 2019

(54) CHART FOR EVALUATING SKIN COLOR AND ITS APPLICATION TO EFFICACY EVALUATION OF ANTI-AGING AND SKIN LIGHTENING PRODUCTS

(71) Applicant: Access Business Group International LLC, Ada, MI (US)

(72) Inventors: Di Qu, Ada, MI (US); Yulia Park, Grand Rapids, MI (US)

(73) Assignee: ACCESS BUSINESS GROUP INTERNATIONAL LLC, Ada, MI (US)

( * ) Notice: Subject to any disclaimer, the term of this patent is extended or adjusted under 35 U.S.C. 154(b) by 48 days.

(21) Appl. No.: 15/359,303

(22) Filed: Nov. 22, 2016

(65) Prior Publication Data

US 2017/0138793 A1    May 18, 2017

Related U.S. Application Data

(62) Division of application No. 14/323,519, filed on Jul. 3, 2014.

(Continued)

(51) Int. Cl.
*G06K 9/00* (2006.01)
*G01J 3/52* (2006.01)
(Continued)

(52) U.S. Cl.
CPC ............ *G01J 3/52* (2013.01); *A61K 49/0006* (2013.01); *G01N 21/251* (2013.01);
(Continued)

(58) Field of Classification Search
CPC .... G06K 9/00281; G06K 9/46; G06T 7/0012; G06T 2207/30201; G06T 2207/10024
See application file for complete search history.

(56) References Cited

U.S. PATENT DOCUMENTS

| 5,311,293 A | 10/1994 | MacFarlane et al. |
| 5,852,675 A | 12/1998 | Matsuo et al. |

(Continued)

FOREIGN PATENT DOCUMENTS

| WO | WO 2005/003700 A1 | 1/2005 |
| WO | WO 2009/059856 A2 | 5/2009 |

OTHER PUBLICATIONS

Weatherall et al.; "Skin color measurements in terms of CIELAB color space values"; Journal of investigative dermatology, vol. 99, Issue 4, Oct. 1992, pp. 468-473.*
Phillips et al., "Efficacy of 0.1 % Tazarotene Cream for the Treatment of Photodamage," *Arch Dermatol*, 138:1486-1493 (2002), (published before this application Nov. 2016).
(Continued)

*Primary Examiner* — Eueng-Nan Yeh
(74) *Attorney, Agent, or Firm* — Brinks Gilson & Lione

(57) ABSTRACT

The present invention relates to charts, stacks and methods for evaluating skin color of a mammalian subject. The chart may include a substrate and an indicia visible from a first side of the substrate that includes a plurality of images of mammalian skin tones having varying degrees of yellowness, wherein each indicia is correlated with an index value. Also, the present invention relates to packaged topical cosmetic products that include a skin chart as well as to methods for evaluating anti-aging and skin lightening products.

12 Claims, 10 Drawing Sheets
(10 of 10 Drawing Sheet(s) Filed in Color)

Human Skin Yellowness Scale Chart
(from 1745 volunteers of various age/ethnicity)

| Skin Yellowness Scale Chart | | | | | | | | |
|---|---|---|---|---|---|---|---|---|
| 1 — 10 point Scale | 2 | 3 | 4 | 5 | 6 | 7 | 8 | 9 |
| L* | 69.9 | 67.9 | 67.9 | 70.2 | 69.6 | 70.0 | 67.9 | 66.3 |
| a* | 14.8 | 15.3 | 15.5 | 14.7 | 14.5 | 14.6 | 15.3 | 15.5 |
| b* | 11.8 | 14.2 | 16.6 | 19.2 | 21.7 | 24.2 | 26.6 | 29.2 |

Related U.S. Application Data

(60) Provisional application No. 61/857,930, filed on Jul. 24, 2013.

(51) Int. Cl.
| | | |
|---|---|---|
| *G06K 15/02* | (2006.01) | |
| *A61K 49/00* | (2006.01) | |
| *G06T 7/90* | (2017.01) | |
| *G01N 21/25* | (2006.01) | |
| *G06K 9/46* | (2006.01) | |
| *G06K 9/62* | (2006.01) | |
| *H04N 1/64* | (2006.01) | |

(52) U.S. Cl.
CPC ....... *G06K 9/00221* (2013.01); *G06K 9/4652* (2013.01); *G06K 9/6298* (2013.01); *G06K 15/1878* (2013.01); *G06T 7/90* (2017.01); *H04N 1/646* (2013.01); *G01N 2201/13* (2013.01); *G06T 2207/10024* (2013.01); *G06T 2207/30201* (2013.01)

(56) References Cited

U.S. PATENT DOCUMENTS

| | | | |
|---|---|---|---|
| 5,858,340 | A | 1/1999 | Briggs et al. |
| 6,549,653 | B1 | 4/2003 | Osawa et al. |
| 6,690,822 | B1 | 2/2004 | Chen et al. |
| 6,766,050 | B1 | 7/2004 | Saikawa et al. |
| 6,888,963 | B2 | 5/2005 | Nichogi |
| 7,010,162 | B2 | 3/2006 | Osawa et al. |
| 7,020,331 | B2 | 3/2006 | Saikawa et al. |
| 7,113,307 | B1 | 9/2006 | Ohkubo |
| 7,136,187 | B1 | 11/2006 | Ohkubo |
| 7,251,362 | B2 | 7/2007 | Osawa et al. |
| 8,319,857 | B2 | 11/2012 | Qu et al. |
| 9,064,279 | B1* | 6/2015 | Tuan ................ G06Q 30/0631 |
| 2002/0122589 | A1 | 9/2002 | Reiman et al. |
| 2003/0065256 | A1 | 4/2003 | Rubinstenn |
| 2004/0261380 | A1 | 12/2004 | Zhaiden et al. |
| 2005/0018226 | A1 | 1/2005 | Chiba |
| 2010/0284610 | A1* | 11/2010 | Yoshikawa ........... G06T 7/0012 382/164 |

OTHER PUBLICATIONS

Tsukahara et al., "A Photographic Scale for the Assessment of Human Facial Wrinkles," *J. Cosmet. Sci.* 51:127-139 (2000), (published before this application Nov. 2016).

Yamamoto et al., "Derivation and Clinical Application of Special Imaging by Means of Digital Cameras and Image J Freeware for Quantification of Erythema and Pigmentation," *Skin Research and Technology*, 14:26-34 (2008), (published before this application Nov. 2016).

Pladellorens et al.,"A Device for the Color Measurement and Detection of Spots on the Skin," *Skin Research and Technology*, 14:65-70, (2008), (published before this application Nov. 2016).

Konishi et al., "New Approach to the Evaluation of Skin Color of Pigmentary Lesions Using Skin Tone Color Scale," *Journal of Dermatology*, 34:441-446 (2007), (published before this application Nov. 2016).

Miyamoto et al., "Development of a Digital Imaging System for Objective Measurement of Hyperpigmented Spots on the Face", *Bioengineering of the Skin: Skin Imaging & Analysis*, Second Edition, 209-219 (2006), (published before this application Nov. 2016).

Coelho et al., "Quantification of UV-Induced Erythema and Pigmentation Using Computer-Assisted Digital Image Evaluation", *Photochemistry and Photobiology*, 82:651-655 (2006), (published before this application Nov. 2016).

Harville et al., "Consistent Image-Based Measurement and Classification of Skin Color", *Hewlett-Packard Laboratories*, HPL-2005-99, May 2005, 5 pages total, (published before this application Nov. 2016).

Kawada et al., "A New Approach to the Evaluation of Whitening Effect of a Cosmetic Using Computer Analysis of Video-Captured Image," *Journal of Dermatological Science*, 29:10-18 (2002), (published before this application Nov. 2016).

Haeghen et al., "An Imaging System With Calibrated Color Image Acquisition for Use in Dermatology", *IEEE Transactions on Medical Imaging*, 19(7):722-730 (2000), (published before this application Nov. 2016).

Chang et al., "RGB Calibration for Color Image Analysis in Machine Vision," *IEEE Transactions on Image Processing*, 5(10): 1414-1422 (1996), (published before this application Nov. 2016).

* cited by examiner

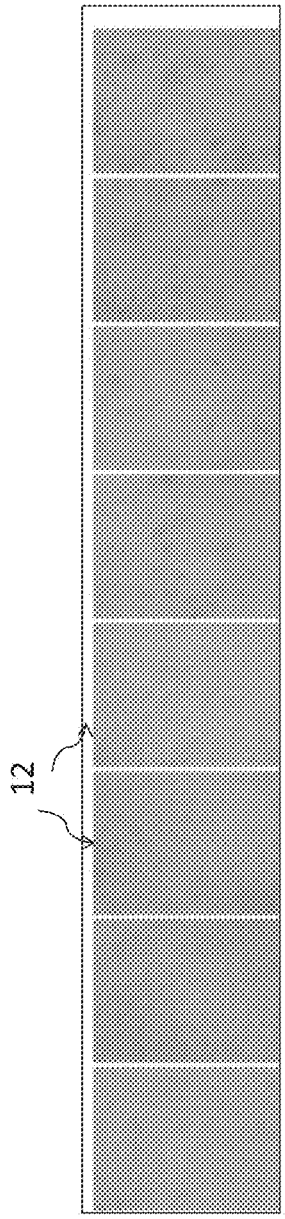
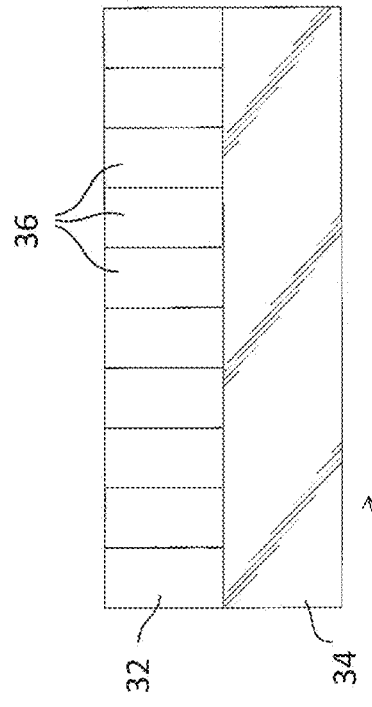
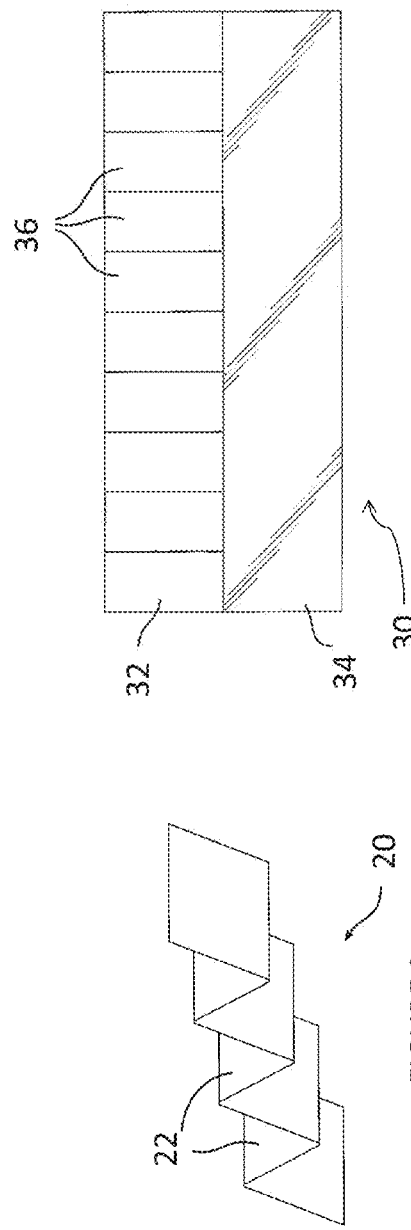
FIGURE 1
FIGURE 2
FIGURE 3

Selection of skin yellowness images for constructing a physical yellowness scale chart Selection of skin yellowness images for constructing a physical yellowness scale chart

| ID | L* | a* | b* | 10 Point Scale |
|---|---|---|---|---|
| 2 | 69.9 | 14.8 | 11.8 | 2.49 |
| 3 | 67.9 | 15.3 | 14.2 | 3.34 |
| 4 | 67.9 | 15.5 | 16.6 | 4.20 |
| 5 | 70.2 | 14.7 | 19.2 | 5.09 |
| 6 | 69.6 | 14.5 | 21.7 | 5.99 |
| 7 | 70.0 | 14.6 | 24.2 | 6.88 |
| 8 | 67.9 | 15.3 | 26.6 | 7.71 |
| 9 | 66.3 | 15.5 | 29.2 | 8.62 |
| average | 68.7 | 15.0 | | |
| max | 70.2 | 15.5 | | |
| min | 66.3 | 14.5 | | |
| s.d. | 1.40 | 0.42 | | |
| range | 3.9 | 1.1 | | |
| %Deviation | 2.82% | 3.51% | | |

- b* → Increasing b* values
- a* → Constant a* values
- L* → Constant L* values

CHART FOR EVALUATING SKIN COLOR AND ITS APPLICATION TO EFFICACY EVALUATION OF ANTI-AGING AND SKIN LIGHTENING PRODUCTS

RELATED APPLICATIONS

The present patent document is a divisional application of U.S. patent application Ser. No. 14/323,519, filed Jul. 3, 2014, which claims the benefit of the filing date under 35 U.S.C. § 119(e) of Provisional U.S. Patent Application Ser. No. 61/857,930, filed Jul. 24, 2013, which is hereby incorporated by reference.

BACKGROUND

The invention relates to a chart and a method for evaluating skin color, such as yellowness in a mammalian subject. The invention further relates to the use of the chart for assessment of skin color changes, for example, in clinical grading and consumer self-assessment of skin improvement or skin color change.

The ultimate goal of a cosmetic composition for skin lightening or anti-aging, as well as that of any other cosmetic product or method, is a satisfied consumer. When using cosmetic skin lightening or anti-aging products, a consumer seeks some degree of visible skin lighting or reduction of age-related skin characteristics, respectively. While many cosmetic products advertise skin lightening or anti-aging benefits, consumers usually cannot easily discern whether the claimed benefit is actually delivered, or a quantitative extent to which it is delivered.

Color instruments are known for color measurements in L*-a*-b* color space according to Commission Internationale de l'Eclairage (CIE) standard. Currently, however, communication with respect to skin yellowness improvement is neither clear nor convenient. Although color instruments are very useful and provide objective data, verbal description is subjective and not accurate. In fact, the yellowness parameter in CIE-LAB color space is rather abstract as it involves a numeric scale range from −50 to 50, representing blue ($b^*=-50$) to yellow ($b^*=50$). In other words, visual assessment is also important in evaluating skin lightening efficacy. After all, it is consumers (human eyes) that evaluate the efficacy or other effect of skin lightening or anti-aging products. Therefore, for visual assessment of color, it is desirable to have a tool as an objective scale for grading.

Phillips et al., "Efficacy of 0.1% Tazarotene Cream for the Treatment of Photodamage," Arch Dermatol, vol 138, p 1486-1493 (November 2002) describes a 5 point scale (0: none −4: severe), noticeable to patients and investigators, for measuring hyper-pigmentation and other conditions. Japan Color Research Institute launched a skin tone color product that can be seen at http://plaza16.mbn.or.ip/~JCRI/seihin/skintone.htm. However, skin texture is not shown in this product, which appears to have simply been based on paints.

A scale for evaluating wrinkles is disclosed in Tsukahara et al., "A Photographic Scale for the Assessment of Human Facial Wrinkles," J. Cosmet. Sci. 51:127-139 (March/April 2000). However, no objective scale for evaluating facial color is reported.

A self-assessment proof strip for evaluating skin lightening progress is discussed in WO 2009/059856. However, the strip for evaluating skin includes images from consumer averaged photographic captured shade batches, which are further "fine-tuned" to match the local populations. The reference does not mention evaluating a specific color of the skin, such yellowness.

Accordingly, there is a need for a tool for the objective visual measurement of attributes of human skin color, especially, for example, yellowness properties of the skin.

SUMMARY

In one embodiment the present invention relates to a chart for evaluating skin color of a mammalian subject including a substrate and an indicia visible from a first side of the substrate and comprising a plurality of images of mammalian skin tones having varying degrees of yellowness, wherein each indicia is correlated with an index value. The number of the images of mammalian skin tones visible from the first side of the substrate may range from two to ten. The chart may include ten images of mammalian skin tones, where a first image corresponds to extremely low yellowness of the skin and a last image corresponds to extremely high yellowness of the skin. The images of mammalian skin tones are replications of facial images from real skin of men and women. The substrate may be paper or a cardboard.

In another embodiment, the present invention relates to a stack of charts for evaluating skin color of a mammalian subject including a plurality of charts, wherein each chart represents a different facial color shade ranging from light- to dark-complexioned facial color and includes a substrate and an indicia visible from a first side of the substrate and comprising a plurality of images of mammalian skin tones having varying degrees of yellowness, wherein each indicia is correlated with an index value. The stack may include from 9 to 18 charts. The stack preferably includes 9 charts.

In yet another embodiment, the present invention relates to a stack of charts for evaluating skin color of a mammalian subject including at least one chart, where the charts includes: a substrate and an indicia visible from a first side of the substrate and comprising a plurality of adjacent rows, each row comprising a plurality of images of mammalian skin tones having varying degrees of yellowness, wherein each indicia is correlated with an index value, and wherein each of the adjacent rows represents a different facial color shade ranging from light- to dark-complexioned facial color. The chart may include from 9 to 18 adjacent rows of images. In the stack, the chart may include 9 adjacent rows of images.

In yet further embodiment, the present invention relates to a packaged topical cosmetic product that includes (i) a topical cosmetic composition comprising an effective amount of an anti-aging or a skin lightning agent and a carrier, (ii) a package for receiving the cosmetic composition, and (iii) one of: (a) a chart for evaluating skin color of a mammalian subject inserted within the package or forming one or more panels of the package, the chart including: a substrate; and the indicia visible from a first side of the substrate and comprising a plurality of images of mammalian skin tones having varying degrees of yellowness, wherein the one or more panels of the package present facial color shades ranging from light- to dark-complexioned facial color; or (b) a stack of charts for evaluating skin color of a mammalian subject comprising a plurality of charts, wherein each chart represents a different facial color shade ranging from light- to dark-complexioned facial color and includes a substrate and an indicia visible from a first side of the substrate and comprising a plurality of images of mammalian skin tones having varying degrees of yellowness, wherein each indicia is correlated with an index value; or (c)

a stack of charts for evaluating skin color of a mammalian subject comprising at least one chart including a substrate an indicia visible from a first side of the substrate and comprising a plurality of adjacent rows, each row comprising a plurality of images of mammalian skin tones having varying degrees of yellowness, wherein each indicia is correlated with an index value, and wherein each of the adjacent rows represents a different facial color shade ranging from light- to dark-complexioned facial color. The number of the images of mammalian skin tones visible from the first side of the substrate can range from 2 to 10. The images of mammalian skin tones may be photographic replications of facial images from real skin of men and women.

In yet another embodiment, the present invention is a method of creating a chart for evaluating skin color of a mammalian subject. The method includes (i) analyzing a plurality of facial images for their color properties: skin brightness ($L^*$), redness ($a^*$), and yellowness ($b^*$); (ii) measuring the $L^*$, $a^*$ and $b^*$ values for each analyzed facial image; (iii) sorting the measured $b^*$ values to show a low-to-high scale; (iv) normalizing the measured $b^*$ values to the +/−4 sigma range to form a distribution of 1-10 point scale; (v) selecting target values for the $L^*$ and $a^*$ values; (vi) selecting facial images that correspond to the distribution of 1-10 point scale, wherein the $a^*$ and the $L^*$ values are target values for the different $b^*$ values at each scale point; and (vii) printing representative facial images corresponding to the distribution of 1-10 point scale onto a substrate. In the method, the target value for $L^*$ may be 69 and the target value for $a^*$ may be 14.8, when choosing various scale points for the $b^*$ values.

In yet further embodiment, the present invention relates to a method for evaluating of anti-aging and skin lightning products. The method includes comparing a skin tone of a subject to a chart as described herein.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1 is an exemplary color chart of the present invention.

FIG. 2 shows one exemplary embodiment of the present invention.

FIG. 3 shows second exemplary embodiment of the present invention.

FIG. 8C shows a selection of the $b^*$ values based on the target $L^*$ and $a^*$ values from FIGS. 8A-B.

DETAILED DESCRIPTION

Figure 4:
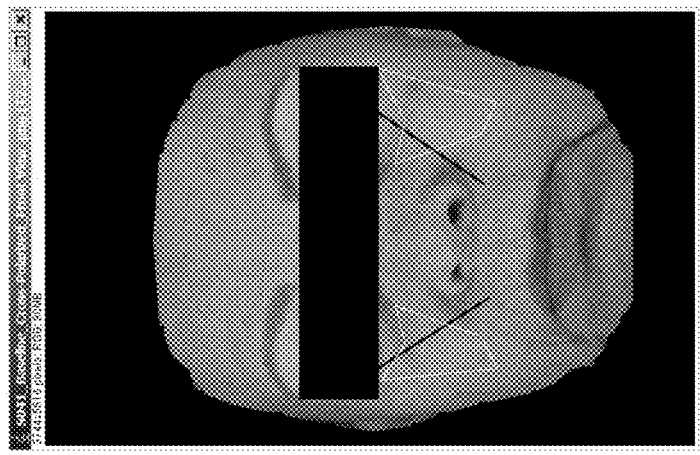
FIG. 4 illustrates methodology for skin color analysis.

The present invention relates to skin color charts and their use in ascertaining facial color changes in mammalian subjects. Specifically, Applicants developed a chart for evaluating skin color, such as e.g., degree of yellowness of the skin of a mammalian subject and methods that can be used (1) as a clinical tool to evaluate the efficacy of skin lightening and/or anti-aging products, (2) as a consumer tool to determine the degree of change that is meaningful and ideal to the consumer, (3) as a consumer clinical tool to measure the effectiveness of products from a consumer and clinical perspective, (4) as a point of purchase device to allow a consumer a simple method to evaluate before and after treatment changes in the skin color and/or yellowness of the skin, (5) as a guide for training external and internal clinical graders, and (6) as standard scale charts for description of human skin yellowness properties in publications, such as books and/or journals.

Applicants developed a color scale chart, system, a packaged topical cosmetic product and methods that provide the ability to define the distribution of skin color in a specific population, set technical and consumer targets, and allows the consumer a simple method to measure the effect. The chart is based on the establishment of a clinical grading scale relevant to consumer perception. Accordingly, the chart of the present invention is a consumer perceivable, clinically usable tool for the assessment of facial skin color. It may be applied for consumer self-evaluation or for evaluation by a clinician, beautician or sales associate.

One advantage of the scale chart of the present invention is that the chart includes photographs of actual skin, so that it looks natural and more like real skin allowing consumers to determine skin color and/or yellowness at any point in time. Skin color determinations may be made in a natural state prior to application of any products and/or for viewing short-term or long-term progress by application of a foundation or make-up and/or measuring progress on efficacy of a cosmetic composition over a prolonged period of use.

Specifically, in one embodiment shown in FIG. 1, the present invention relates to a scale chart 10 for evaluating skin color, e.g., yellowness in a mammalian subject that includes a substrate and an indicia visible from a first side of the substrate and including a plurality of images 12 of mammalian skin tones having varying degrees of yellowness, where each indicia is correlated with an index value.

The term "cosmetic composition" is intended to describe compositions for topical application to human skin, including leave-on and wash-off products.

The term "skin" refers to the skin on the face, neck, chest, back, torso, arms, axillae, hands, legs, and scalp.

The term "indicia" refers to a printed marking(s) on a substrate or a package.

The term "index value" refers to a known value that corresponds to a color on a color scale chart.

The term "color" is a general term intended to cover human perception of color and includes variations in lightness/darkness and/or variations in hue or skin tone.

"Brightness" is defined in terms of the $L^*$ parameter in the $L^*$-$a^*$-$b^*$ color space. The greater the $L^*$ value, the lighter the skin. The smaller the L* value, the darker the skin, indicating higher melanin content.

"Hue" is defined as the color component on a red to yellow spectrum. On the color ruler, hue is defined in terms of the a* and b* parameters in L*-a*-b* color space, as follows: Hue=$\tan^1$ (b*/a*).

Redness is defined as a*.

The term "yellowness" refers to a degree of the yellow color in the skin tone of an individual. Yellowness is defined as a b* value. The higher the b* value, the more yellow tones are present in the skin.

Usually for skin color, a* and b* are greater than zero.

In certain embodiments, the present invention relates to a color chart for assessing attributes of skin color, and specifically, for assessing the yellowness properties on an area of human skin. In a preferred embodiment, the color chart of the present invention includes at least two images and can contain a plurality of images. It is, however, preferred that the number of images be between two and ten (where scales 1 and 10 may be designed to represent the extreme conditions, very less yellow or extremely yellow); more preferably, the color chart includes eight images; most preferably, the number of images is ten.

A database of images from more than twenty one thousand people around the world was used to create a color chart of the present invention. The database enabled a selection of skin images at various yellowness (b*) values while keeping the L* and a* values relatively constant.

Specifically, one thousand seven hundred forty five facial images were first analyzed for their color properties. Areas of the skin shown in FIG. 4 were analyzed. Two areas of face, one on each cheek, were used for this analysis, as highlighted by the areas with yellow borders in FIG. 4. The L*a*b* values were average values of those two cheek areas on each image. Typically, during image analysis, each individual image was first color-corrected using the color stripe embedded in the image and an in-house developed color correction algorithm (U.S. Pat. No. 8,319,857, which is incorporated herein in its entirety). Then, the key features on the face, such as the corners of eyes, mouth, and eyebrows, may be detected using an in-house developed image analysis algorithms. Those features served as reference points to draw regions of interests (ROI) on the face for color analysis. Average R, G, and B values in each ROI may be measured and eventually may be converted to L*, a* and b* values.

Figure 5:
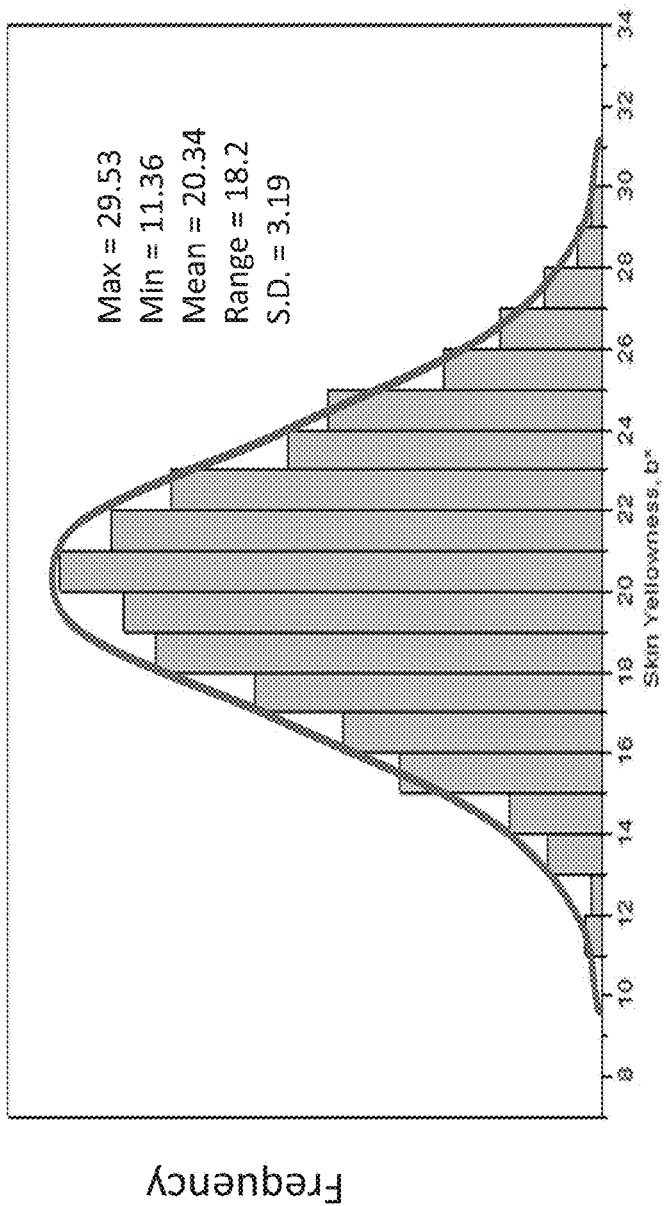
FIG. 5 depicts a graph showing a distribution of human skin yellowness among female subjects ages 20-70 years old.
Figure 6:
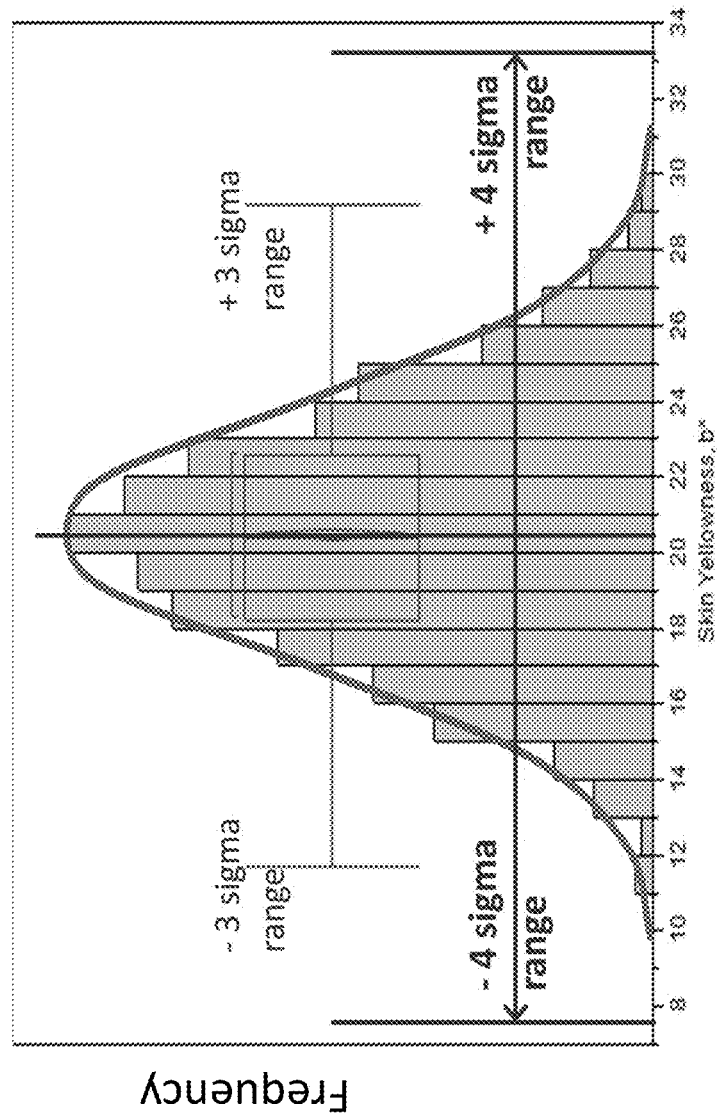
FIG. 6 depicts a graph showing a protocol for extending the $b^*$ value distribution to a +/−4 sigma range.
Figure 7:
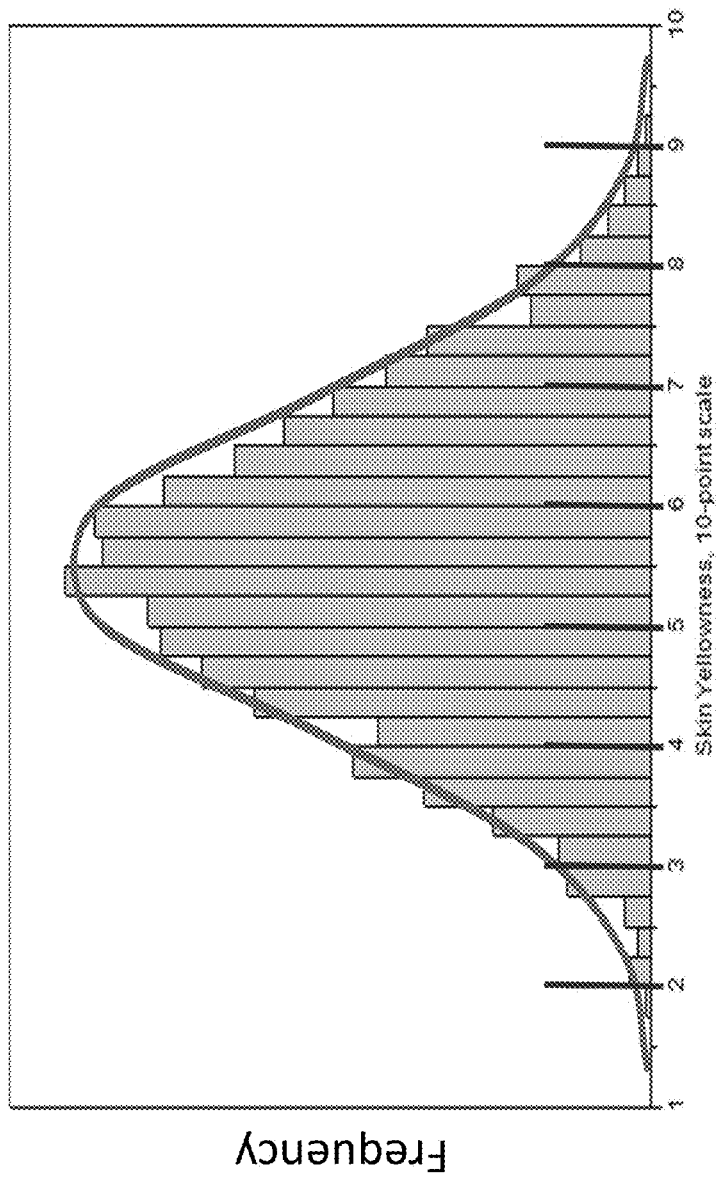
FIG. 7 depicts a graph showing a normalizing procedure for the $b^*$ values to the +/− sigma range to form a new distribution of 1-10 scale.

The results were expressed as the skin brightness (L*), redness (a*), and yellowness (b*) values. The b* values were then sorted to show a low-to-high-scale, as seen in FIG. 5. With statistical analysis, the plus or minus 4-sigma distribution of the studied population was found, which extended the original distribution of the b* values from a range of 11.356-29.530 to a wider range of 7.662-33.198, as shown in FIG. 6. The new, wider range provided an adequate color space to encompass any skin yellowness values that were encountered or that may be encountered. As shown in FIG. 7, each data point was then normalized to the new range to capture a skin yellowness distribution in a 10-point scale range with the actual distribution limits from 1 to 10, which presents a simple scale that can be easily understood by the consumers.

Image Selection Protocol.

Figure 9:
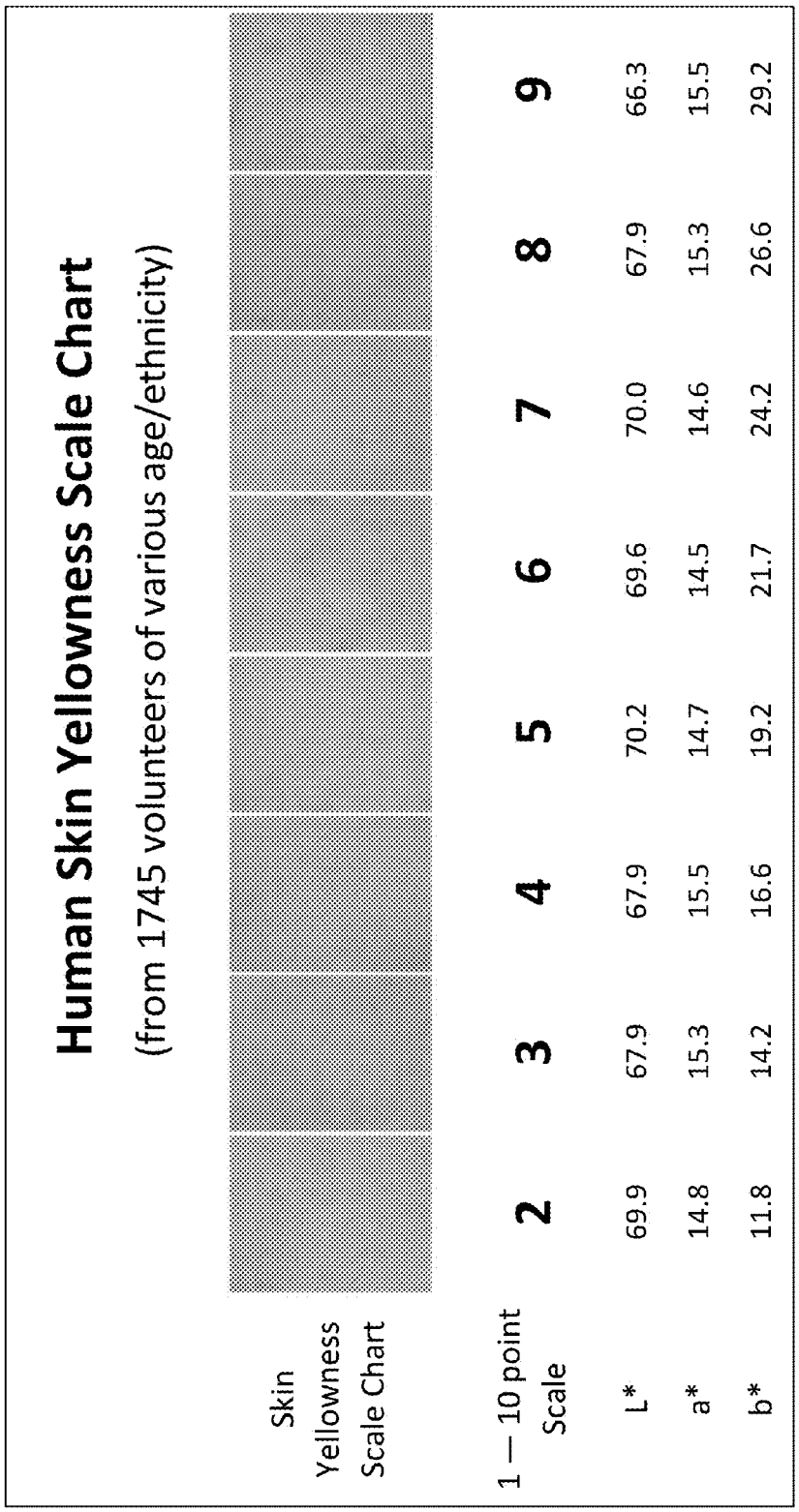
FIG. 9 depicts an exemplary skin yellowness scale chart.

The selection of images for each scale point of the color chart consisted of the following steps:

(1) Select facial images that scored close to the whole number points (e.g., 2, 3, 4, . . . 9, etc.) from the 10-point yellowness chart shown in FIG. 9 (i.e., correlating to the index value);

(2) Look at the corresponding L* and a* values of each image; and (3) Keep the L* and a* values relatively constant for different b* values at each point of the chart.

Figures 8A, 8B:
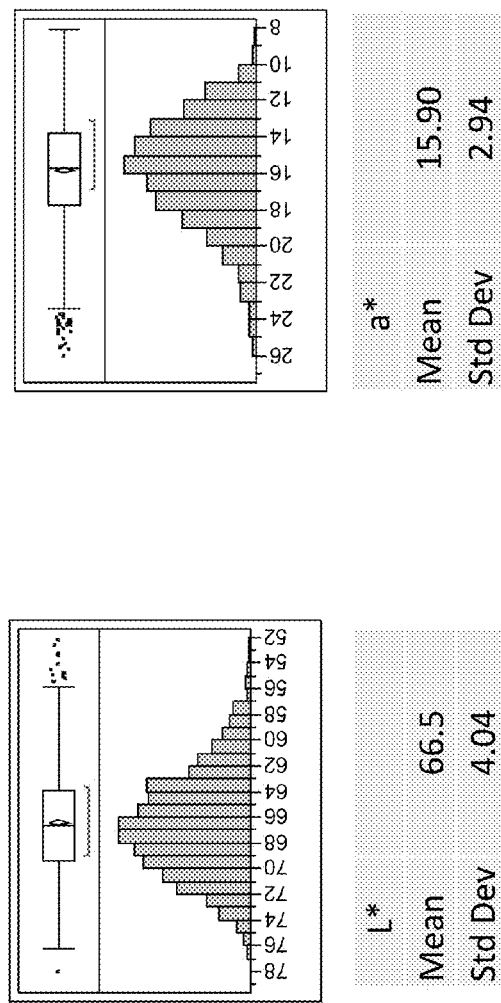
FIG. 8A depicts a graph showing a value distribution for the $L^*$ values.
FIG. 8B depicts a graph showing a value distribution for the $a^*$ values.

For instance, the target value for the L* and a* was 69 and 14.8 (FIG. 8A-B), respectively, when choosing various scale values for b*. The preferred variation in L* and a* values for the selected b* values was less than 1.5 standard deviation, most preferably, between 0.5 to 1.5, and most preferably, less than 0.5. So among many b* values close to each scale point, the image having: (a) the a* values of the selected image as close to the target value (a*=14.8); (b) the L*value of the selected image as close to the target value (L*=69); and (c) the b* value of the selected image as close to a selected scale point (e.g., b*=5) was selected. The preferred variation in L* and a* values for the selected b* values should be less than 1.5 standard deviation, most preferably, between 0.5 to 1.5, and ideally, less than 0.5.

With the above criteria, 8-10 images can be selected from the available facial images database. Properties of the selected facial images are listed in Table 1 below (FIG. 8C). The corresponding images are shown in FIG. 9. These photos were good for capturing overall distribution of skin color.

TABLE 1

| ID | L* | a* | b* | 10 Point Scale |
|---|---|---|---|---|
| 2 | 69.9 | 14.8 | 11.8 | 2.49 |
| 3 | 67.9 | 15.3 | 14.2 | 3.34 |
| 4 | 67.9 | 15.5 | 16.6 | 4.20 |
| 5 | 70.2 | 14.7 | 19.2 | 5.09 |
| 6 | 69.6 | 14.5 | 21.7 | 5.99 |
| 7 | 70.0 | 14.6 | 24.2 | 6.88 |
| 8 | 67.9 | 15.3 | 26.6 | 7.71 |
| 9 | 66.3 | 15.5 | 29.2 | 8.62 |
| Average | 68.7 | 15.0 | | |
| Max | 70.2 | 15.5 | | |
| Min | 66.3 | 14.5 | | |
| s.d. | 1.40 | 0.42 | | |
| Range | 3.9 | 1.1 | | |
| % Deviation | 2.82% | 3.51% | | |

As discussed above, the color scale chart of the present invention includes a substrate and an indicia visible from a first side of the substrate and comprising a plurality of images of mammalian skin tones having varying degrees of yellowness, wherein each indicia is correlated with an index value in order to allow visual assessment of skin color.

In certain embodiments, the scale chart may also be captured in a medium, such as computer, Internet, camera, personal digital assistant (e.g. Palm™ Pilot), mobile phone, water-insoluble substrate, or advertising and promotional material including television, magazines, brochures, posters, flyers, and hand-outs.

Several possible embodiments of the color chart of the present invention having a substrate and an indicia visible from a first side of the substrate and comprising a plurality of images of mammalian skin tones having varying degrees of yellowness, wherein each indicia is correlated with an index value, are as follows.

With reference to FIG. 9, in one embodiment of the present invention, the chart includes a substrate and an indicia visible from a first side of the substrate. The indicia includes a plurality of images of mammalian skin tones (e.g., in a single row) having varying degrees of yellowness, wherein each indicia is correlated with an index value. The degree of yellowness may increase from one image to the next adjacent image.

Suitable materials for the substrate are paper (e.g., general writing or copy paper), cardboard (such as, e.g., seen in cosmetic packaging), and plastics or cellulosics of any variety thereof which can be formed as transparent films. In certain embodiments, paper materials include gloss or "half-gloss" photographic paper.

The size of the chart can be flexible, suitable for inserting into a skin care product package or printing on a skin care package, or for a clinical grader to conveniently carry and reference during a clinical study.

When the substrate is made of plastic, typically the plastic may be selected from polyethylene, polypropylene, polystyrene, polyester, polycarbonate, polyacrylate, polyvinyl chloride, polyvinyl alcohol and polybutene. Not only homopolymers but copolymers may be utilized for the strip material. Copolymers may be formed from such monomers as $C_2$-$C_{10}$ olefins, vinyl chloride, acrylates and styrene constructed through free-radical polymerization. Condensation plastics may also be utilized in the formation of copolymers wherein the monomers may be selected from $C_2$-$C_{10}$ dicarboxylic acids, $C_2$-$C_{10}$ polyols, $C_2$-$C_6$ alkoxylates and combinations thereof. Polyethylene, polypropylene and polyester terephthalate are the preferred plastic substrates for forming the strip.

The substrate may also include ceramic material, such as tiles and back-lit illumination systems with cellulose and glass.

The substrate of the color chart of the present invention may be made of combinations of the materials above.

The thickness of the substrate may range anywhere from about 0.00001 to about 2 mm, preferably from about 0.0001 to about 1 mm, more preferably from about 0.001 to about 0.5 mm and optimally from about 0.01 to about 0.1 mm.

To create the indicia, print is placed onto a selected side of the substrate. Normally the print will be combinations of colored ink, and ordinarily a four-color process. The printing procedure is not critical and will be known to those skilled in the art. Typical processes include lithography, gravure, flexography, letterpress and screen processes. Of particular usefulness are thermal printing, electrophotography and inkjet printing. The inks are normally formed of a colored pigment, resin binder and, most frequently, a volatile solvent.

In one embodiment, the chart may be printed with a single row of images of mammalian skin tones having varying degrees of yellowness, where the degree of yellowness increases from one image to the next adjacent image (FIG. 1).

The spacing of the facial images on the substrate is based on how humans perceive the skin color, and especially skin yellowness. Therefore, in one embodiment, the preferred scale for the chart is a 10-point scale. The preferred increment in the scale is 1 with values in whole numbers. As such, the number of the images of mammalian skin tones visible from the first side of the substrate can range from 2 to 9. In one preferred embodiment, the chart includes 10 images of mammalian skin tones, where a first image corresponds to extremely low yellowness of the skin and a last image corresponds to extremely high yellowness of the skin. The images of mammalian skin tones are replications of facial images from real skin of men and women.

Progressively, the images of the mammalian skin tones on the charts become more yellow, where yellowness increases from a first image to the next adjacent image in the row. In other words, the first image on the scale chart corresponds to extremely low yellowness and the last image on the scale chart corresponds to extremely high yellowness of the skin.

Since the redness and brightness of general population vary significantly, charts at various redness (a*) and brightness (L*) combinations for evaluating skin color, and especially for evaluating the yellowness of the skin according to the methods of the present invention, are necessary to accommodate the needs of various ethnic and racial groups or individuals.

The ethnic groups or races may include Hispanic/Latino (Cuban, Mexican, Puerto Rican, South or Central American, or other Spanish culture or origin); American Indian/Alaska Native; Asian (origin in any peoples of the Far East, Southeast Asia, or the Indian Islands, Thailand and Vietnam); Black/African American (persons having origins in any of the black racial groups of Africa); Native Hawaiian/other Pacific Islander (persons having origins in any of the original peoples of Hawaii, Guam, Samoa, or other Pacific Islands); and White (a person having origins in any of the original peoples of Europe, the Middle East, or North Africa).

To take into account the variability in skin color between different ethnic and racial groups or individuals, the charts may be designed as "stacks" that include: (i) at least one chart that includes: a substrate, and an indicia visible from a first side of the substrate, and comprising a plurality of adjacent rows of images of mammalian skin tones, each row including a plurality of images of mammalian skin tones having varying degrees of yellowness, wherein each of the adjacent rows represents a different facial color shade ranging from light- to dark-complexioned facial color, and wherein each indicia is correlated with an index value; or (ii) a plurality of charts, where each chart represents a different facial color shade ranging from light- to dark-complexioned facial color, and includes: a substrate, and an indicia visible from a first side of the substrate and comprising a plurality of images of mammalian skin tones having varying degrees of yellowness, wherein each indicia is correlated with an index value.

The term "stack" refers to (i) a plurality of color scale charts combined or attached together in a suitable manner, where each chart in the stack represents a different facial color shade ranging from light- to dark-complexioned facial color, or (ii) to a single chart that includes a plurality of adjacent rows of facial images, where each of the adjacent rows of images represents a different facial color shade ranging from light- to dark-complexioned facial color.

The range of the brightness is preferably from L*=52 to L*=78, and for the redness from a*=10 to a*=20. The number of combinations of L* and a* is preferably from 9 to 18, and most preferably 9. As such, in certain embodiments, the stack can include a chart with 9 to 18, or preferably 9 adjacent rows of images, or 9-18, or preferably 9 separate charts in the stack.

The indicia containing facial images may be printed on individual strips of substrate, where the indicia can include a single row of facial images per each strip of substrate. Alternatively, the indicia can include a plurality of rows of facial images per each strip of substrate. The plurality of charts, whether containing a single or a plurality of rows per each of the strips of the substrate, form a "stack" of charts for evaluating skin color of a mammalian subject, such as the yellowness of the skin of the mammalian subject.

For example, as mentioned above, in one embodiment, the chart may be printed with two or more adjacent rows of images of mammalian skin tones having varying degrees of yellowness, where the degree of yellowness increases from one image to the next adjacent image. The adjacent rows may differ by having varying a* and L* combinations to accommodate differences in ethnic and racial skin tone differences. For example, the first row of facial images may be suitable for evaluating Asian-origin skin tones, the second row of facial images may be suitable for evaluating Caucasian-origin skin tones, the third row may be suitable for evaluating Hispanic/Latino-origin skin tones, etc.

Similar to the single-row chart, the number of the images of mammalian skin tones visible from the first side of the substrate in the stack can range from 2 to 9 per row. In a preferred embodiment, the chart includes 8 images of mammalian skin tones per each row of images, where a first image in the row corresponds to extremely low yellowness of the skin and a last image in the row corresponds to extremely high yellowness of the skin. The images of mammalian skin tones are replications of facial images from real skin of men and women.

Referring to FIG. 3, in certain embodiments, the chart 30 may further include a transparent and/or mirrored surface or other reflective surface 34, advantageously eliminating the need for a user to find a mirror. In use, a user may place the chart containing a transparent surface 34 against their skin and compare their skin to scale 32 while looking in a mirror. In the case of a reflective surface 34, a user may look into the reflective surface 34 and compare their skin in the reflective surface 34 against scale 32. The scale of mammalian skin tones is shown with 36.

Cosmetic Compositions

In yet another embodiment, the present invention relates to a packaged topical cosmetic product. The packaged cosmetic product includes a topical cosmetic composition that includes an effective amount of an anti-aging or a skin lightning agent and a carrier. The packaged cosmetic product also includes a package for receiving the cosmetic composition, and at least one of (i) a chart for evaluating skin color of a mammalian subject, and (ii) a stack of charts for evaluating the skin color of a mammalian subject.

In certain embodiments, the color scale chart may be folded into a concertina, or accordion arrangement, or another suitable shape, for compactness and/or easier insertion onto a package (FIG. 2). The images of mammalian skin tones 22 are visible from the first side of the substrate. The package may be made from the same materials listed above in connection with the substrate. In a preferred embodiment, the package is made from a cardboard material. The scale chart for use with the illustrated embodiment will allow observation and comparison of the condition of skin color with the color chart of the present invention.

The topical cosmetic compositions according to the present invention may be in the form of creams, lotions, toners, pastes, sticks (e.g. concealer sticks), or powders. These cosmetics will, normally, include a carrier.

Suitable carriers include water, emollients (esters, hydrocarbons, silicones, polyols and mixtures thereof), emulsifiers, thickeners and combinations thereof. Most often the carrier will be an emulsion such as an oil-in-water or water-in-oil type. Amounts of the carrier may range from about 1 to about 99.9% by weight.

Exemplary skin lightening agents or actives include kojic acid and esters, ferulic acid and ferulate derivatives, vanillic acid and esters, dioic acids (such as sebacic and azoleic acids) and esters, retinol, retinal, retinyl esters, hydroquinone, t-butyl hydroquinone, mulberry extract, licorice extract, and resorcinol derivatives, especially 4-substituted resorcinol derivatives.

Exemplary anti-aging agents or additives may include retinoids, ceramides, alpha or beta-hydroxycarboxylic acids, flavonoids, vitamins, sunscreens, anti-oxidants, preservatives and mixtures thereof.

Typical retinoids include retinol, retinoic acid and retinol esters. The latter include retinyl palmitate, retinyl linoleate, retinyl propionate* retinyl acetate and retinyl salicylate.

Alpha-hydroxy acids include the free acid, lactone and salt forms of glycolic acid, lactic acid, citric acid, gluconolactone, glucarolactone, tartaric acid, malic acid and mixtures thereof. Beta-hydroxycarboxylic acids are exemplified by salicylic acid as well as its esters (e.g. tridecylsalicylate) and salts including ammonium, aikanolammonium and alkalimetal salts.

Ceramides include Ceramide 1, Ceramide 2, Ceramide 3, Ceramide 3a, Ceramide 3b, Ceramide 4, Ceramide 5 and Ceramide 6, as well as pseudoceramides, phytosphingosines and tetraacetyl phytosphingosine.

Vitamins may include ascorbic acid as well as its water-soluble and water-insoluble derivatives. Illustrative examples include ascorbyl tetraisopalmitate, magnesium ascorbyl phosphate and ascorbyl glucoside. Other vitamins include Vitamin B3 (niacin, niacinamide and panthenol), biotin, folic acid, tocopherol and its esters (e.g. tocopherol isopalmitate), Vitamin D and combinations thereof.

Antioxidants include BHT (butylated hydroxytoluene), BHA (butylated hydroxyanisole), disodium EDTA (available from Ciba), sodium citrate, hydroquinone, ferulic acid and esters thereof, green tea extract, lipoic acid, N-acetyl cysteine, resveratrol and combinations thereof.

The following additional skin benefit agents may optionally be used and include: astringents, humectants, acne and sebum suppressants, desquamation enhancers, keratolytics, and make-up, among other pore reduction actives known to one skilled in the art.

Examples of astringents include ethanol, witch hazel, zinc and aluminum salts, and polyphenols.

Humectants include propylene glycol (available from Spectrum) glycerol, and sorbitol, among other humectants known to one skilled in the art. Humectants are known as excellent moisturizers for skin, scalp and hair. See for instance, U.S. Pat. No. 5,858,340, incorporated by reference herein.

Other skin benefit agents may be included as optional components and would be known to one of skill in the art.

Amounts of skin lightening or anti-aging actives may range anywhere from 0.0000001 to 30%, preferably from 0.0001 to 15%, more preferably from 0.1 to 5%, by weight. Other percentages of actives may also be used, if necessary and/or desirable.

A variety of packaging arrangements is envisioned and will be known to a skilled in the art. The color chart of the present invention may be printed on the primary or secondary packaging.

Methods of Use

The inventive scale chart, stack, packaged topical cosmetic product, and methods can be used (1) as a clinical tool to evaluate the efficacy of skin lightening and/or anti-aging products, (2) as a consumer tool to determine the degree of change that is meaningful and ideal to the consumer, (3) as a consumer clinical tool to measure the effectiveness of products from a consumer and clinical perspective, (4) as a point of purchase device to allow a consumer a simple method to evaluate before and after treatment changes in skin color, and (5) as a standard scale chart for the description of human skin yellowness in publications (books, journal articles, internet articles, etc.).

The color scale chart of the present invention provides the ability to define the distribution of skin color in a specific population, set technical and consumer targets, and allows the consumer a simple method to self-assess the effect. Specifically, the color chart may be used for determining the condition of skin color pre- and/or post-treatment or cosmetic product application, or to track changes in skin color, especially the degree of yellowness of skin, associated with a variety of factors, such as cosmetic product usage and/or sun exposure.

Pre-treatment color chart measurements may be used to select an appropriate cosmetic product. For example, different product formulations may be recommended depending on the individual condition as measured on the color chart. Color chart indicia may be printed directly on the package for this purpose, or represented in other media within the scope of the present invention.

Subsequent to a baseline analysis of skin on the color chart, a make-up product can be applied and/or treatment can begin with a selected cosmetic product for skin lightening and/or skin anti-aging. Treatment is continued for a period of time sufficient to allow the product to lighten the skin or improve the skin appearance. The term "improve skin appearance" refers to prevention and/or reduction of wrinkles, prevention or reduction of appearance of age spots and or fine lines, reduction of yellowness in skin tone, etc.

After the treatment period, such as, for example, two weeks or four weeks or 6 weeks, or longer, another color chart measurement can be taken.

Testing may occur thereafter at 8, 12, 16 and/or 20 weeks. The time intervals and numbers may be longer or shorter. If the cosmetic product is properly functioning, skin will appear lighter (or less yellow), or younger on the color chart and the color chart score will be lower. This procedure can then be repeated at six or eight weeks or at any further time interval. Each test may employ the same or a fresh color chart or a chart medium.

The color chart may be used in conjunction with a variety of media for displaying or embodying the color chart scale. These media include in or out of home use of strips as described hereinabove, the computer, Internet, webcam, palm pilot, mobile phone, and other media capable of displaying the color chart scale. A color chart scale of at least 2 points and as many as 6 to 9 or more points may be printed directly on the package. A strip embodying a color chart scale may be given out to consumers at point of sale or at a store display.

In another embodiment, the color chart may be used as a clinical tool to set lightening or brightening or anti-aging goals and/or to support skin lightening or anti-aging product claims on the package. The color chart may also be used by beauticians and make-up artists to select an appropriate foundation or other make-up application. The color chart provides a clinical grading scale, whereby each image is associated with a numerical scale. Except in the operating and comparative examples, or where otherwise explicitly indicated, all numbers in this description indicating amounts of material ought to be understood as modified by the word "about."

For the avoidance of doubt, the term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

EXAMPLES

Example 1

This example illustrates that evaluation of pre- and post-treatment skin color is possible using the color scale chart of the present invention, suggesting the validity and usefulness of the color scale chart and methods of the present invention.

Figure 10A:
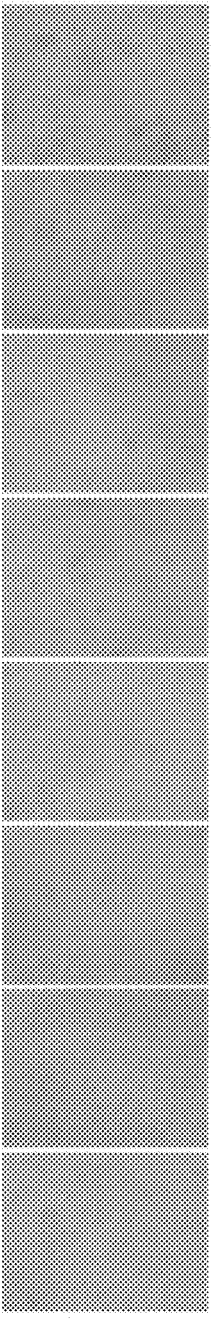
FIG. 10A depict skin yellowness chart for evaluating yellowness.

A cosmetic formulation for improving skin yellowness was evaluated using an 8-point scale on the color chart shown in FIG. 10A.

Figure 10B:
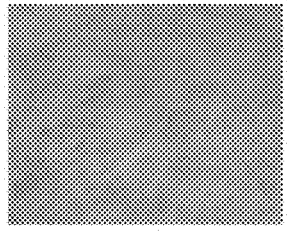
FIG. 10B depicts the initial skin color of a subject under evaluation.
Figure 10C:
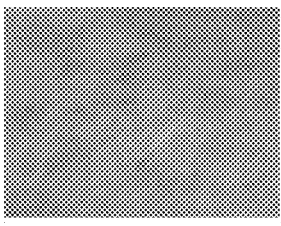
FIG. 10C depicts the skin color of a subject following a treatment.

The initial skin color of a subject is shown in FIG. 10B, where the baseline was 5.98 ($b^*$=21.63). The results were obtained following the prescribed time period for the treatment of 12 weeks with the cosmetic formulation and are shown in FIG. 10C, where the score was 4.61 ($b^*$=18.16). The color chart score showed improvement from almost 6 to 4. As such, a 22.9% improvement over baseline was observed using the color chart.

Example 2

This example illustrates that consumers are able to perceive the yellowness color difference between the skin images on the 8-image color chart of the 10-point scale of the present invention. This validates the suggested skin yellowness scale as consumer-relevant.

Figure 11:
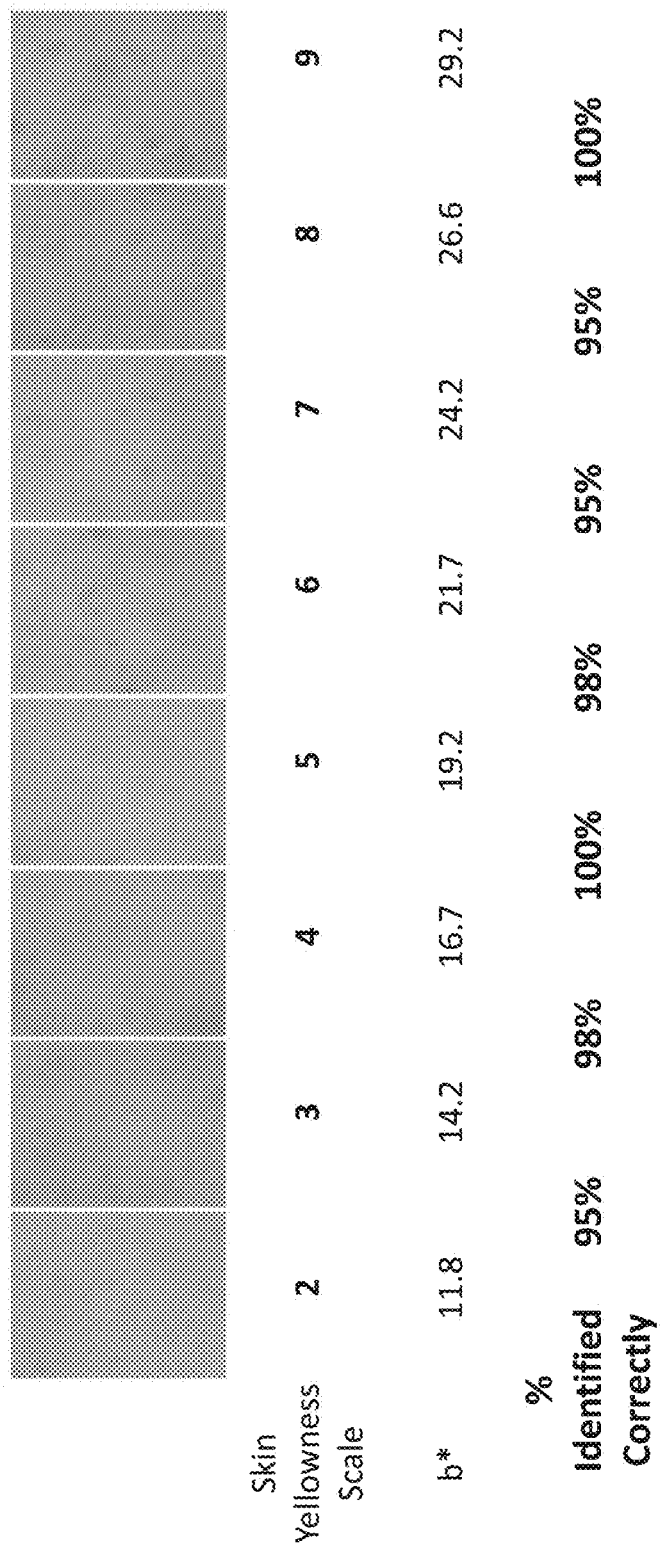
FIG. 11 depicts consumer perception of skin yellowness scale.

A skin yellowness 8-image color chart shown in FIG. 11 was used in this study.

Images shown on the chart were displayed on a color-corrected monitor in an imaging lab for consumer evaluation. Adjacent images on the chart were presented in pairs, i.e. images 2 and 3, images 3 and 4, etc., one pair at a time for the total of 7 pairs. Presentation order of the pairs was randomized and the position of images in the pair (left and right on the screen) was randomized as well.

Forty one respondents of random age and gender were presented with one pair of images at a time and asked to click on the "more yellow" of the two skin images.

The results of the study are shown in FIG. 11, where "Percent identified correctly" corresponds to the percent of respondents that were able to correctly pick the image with higher $b^*$ value as "the more yellow" in the pair. 2% error indicates that 1 person of 41 misidentified the images in the pair; 5% error corresponds to 2 people of 41 that misidentified the images in the pair.

This study demonstrated that a majority of people tested were able to correctly perceive the slight yellowness differences between the adjacent images on the color chart in FIG. 11 therefore validating the consumer significance of the proposed 10-point skin yellowness scale.

All parts, percentages and proportions referred to herein and in the appended claims are by weight unless otherwise illustrated.

The invention claimed is:

1. A method of creating a chart comprising:
   (i) analyzing a plurality of facial images for their color properties: skin brightness ($L^*$), redness ($a^*$), and yellowness ($b^*$);
   (ii) measuring the $L^*$, $a^*$ and $b^*$ values for each analyzed facial image;
   (iii) sorting the measured $b^*$ values to show a low-to-high scale;

(iv) normalizing the measured b* values to the +/−4 sigma range to form a skin yellowness distribution of 1-10 point scale range;

(v) selecting L* and a* values of interest from the measured L* and a* values;

(vi) selecting facial images that correspond to the skin yellowness distribution of 1-10 point scale range, wherein the selected a* and the L* values are target values for the different b* values at each scale point;

(vii) printing representative facial images corresponding to the skin yellowness distribution of 1-10 point scale onto a substrate.

2. The method of claim 1, wherein the target value for L* is 69 and the target value for a* is 14.8 when choosing various scale points for the b* values.

3. The method of claim 1, wherein the chart is for evaluating of anti-aging and skin lightning products by comparing a skin tone of a mammalian subject to the chart.

4. The method of claim 1, wherein the chart is for evaluating skin color of a mammalian subject.

5. The method of claim 1, wherein the chart is for evaluating skin yellowness of a mammalian subject.

6. The method of claim 1, wherein the step (vi) comprises selecting the images as follows:
   a first image having L*=69.9, a*=14.8 and b*=11.8;
   a second image having L*=67.9, a*=15.3 and b*=14.2;
   a third image having L*=67.9, a*=15.5 and b*=16.6;
   a fourth image having L*=70.2, a*=14.7 and b*=19.2;
   a fifth image having L*=69.6, a*=14.5 and b*=21.7;
   a sixth image having L*=70.0, a*=14.6 and b*=24.2;
   a seventh image having L*=67.9, a*=15.3 and b*=26.6; and
   an eighth image having L*=66.3, a*=15.5 and b*=29.2.

7. The method of claim 1, wherein the point scale of 1-10 includes 10 images of mammalian skin tones, wherein a first image corresponds to extremely low yellowness of the skin and a last image corresponds to extremely high yellowness of the skin.

8. The method of claim 1, wherein the printed representative facial images are replications of facial images from real skin of men and women.

9. The method of claim 1, wherein the substrate is paper or a cardboard.

10. The method of claim 1, wherein the step (i) comprises analyzing two areas of face and one area on each cheek for each facial image.

11. A method of creating a chart for evaluating skin color of a mammalian subject comprising:
   (i) analyzing a plurality of facial images for their color properties: skin brightness (L*), redness (a*), and yellowness (b*);
   (ii) measuring the L*, a* and b* values for each analyzed facial image;
   (iii) sorting the measured b* values to show a low-to-high scale;
   (iv) normalizing the measured b* values to the +/−4 sigma range to form a distribution of 1-10 point scale;
   (v) selecting L* and a* values of interest from the measured L* and a* values;
   (vi) selecting facial images that correspond to the distribution of 1-10 point scale, wherein the selected a* and the L* values are target values for the different b* values at each scale point;
   (vii) printing representative facial images corresponding to the distribution of 1-10 point scale onto a substrate;
   wherein the chart comprises the substrate and at least one indicia visible from a first side of the substrate and comprising a plurality of photographic images of mammalian skin tones having varying degrees of yellowness, wherein the yellowness increases from a first image to an adjacent image, wherein each indicia is correlated with an index value,
   wherein the chart allows for evaluation of skin color to determine a degree of yellowness in the subject's skin by comparing the subject's skin to each image of the indicia.

12. The method of claim 11, wherein the step (vi) comprises selecting the images as follows:
   a first image having L*=69.9, a*=14.8 and b*=11.8;
   a second image having L*=67.9, a*=15.3 and b*=14.2;
   a third image having L*=67.9, a*=15.5 and b*=16.6;
   a fourth image having L*=70.2, a*=14.7 and b*=19.2;
   a fifth image having L*=69.6, a*=14.5 and b*=21.7;
   a sixth image having L*=70.0, a*=14.6 and b*=24.2;
   a seventh image having L*=67.9, a*=15.3 and b*=26.6; and
   an eighth image having L*=66.3, a*=15.5 and b*=29.2.

* * * * *